United States Patent
Turcot et al.

(10) Patent No.: US 7,588,720 B2
(45) Date of Patent: Sep. 15, 2009

(54) METHOD AND APPARATUS FOR OZONE STERILIZATION

(75) Inventors: Richard Turcot, Cap Rouge (CA); Simon Robitaille, Charny (CA); Sylvie Dufresne, Cap Rouge (CA)

(73) Assignee: TSO3, Inc., Sainte-Foy, Quebec (CA)

( * ) Notice: Subject to any disclaimer, the term of this patent is extended or adjusted under 35 U.S.C. 154(b) by 159 days.

(21) Appl. No.: 11/554,763

(22) Filed: Oct. 31, 2006

(65) Prior Publication Data

US 2007/0258855 A1 Nov. 8, 2007

Related U.S. Application Data

(63) Continuation-in-part of application No. 10/005,786, filed on Nov. 8, 2001, now Pat. No. 7,128,872, which is a continuation-in-part of application No. 09/310,695, filed on May 12, 1999, now abandoned.

(30) Foreign Application Priority Data

Apr. 30, 1999 (CA) .................................. 2270512

(51) Int. Cl.
- A61L 9/00 (2006.01)
- A61L 2/00 (2006.01)
- A62B 7/08 (2006.01)
- B01J 19/08 (2006.01)
- C01B 13/10 (2006.01)
- C25C 1/00 (2006.01)
- C02F 1/461 (2006.01)

(52) U.S. Cl. .................. 422/1; 422/4; 422/22; 422/24; 422/28; 422/105; 422/121; 422/122; 422/123; 422/186; 422/186.08; 422/33; 422/186.07; 422/292; 422/295; 422/296; 422/305; 422/906; 422/907; 422/116; 204/176; 204/194; 205/626; 205/334; 205/752; 205/756; 205/615

(58) Field of Classification Search ..................... 422/1, 422/4, 22, 24, 28, 105, 121–123, 186, 186.08, 422/33, 186.07, 292, 295–296, 305, 906–907, 422/116; 204/176, 194; 205/626, 334, 752, 205/756, 615

See application file for complete search history.

(56) References Cited

U.S. PATENT DOCUMENTS 3,719,017 A 3/1973 Shapiro (Continued)

FOREIGN PATENT DOCUMENTS

CA 2466307 5/2003

(Continued)

*Primary Examiner*—Jill Warden
*Assistant Examiner*—Monzer R Chorbaji
(74) *Attorney, Agent, or Firm*—Novak Druce + Quigg; Jerold I. Schneider; Gregory M. Lefkowitz

(57) ABSTRACT

The present invention provides a method and apparatus for sterilizing articles using an ozone-containing gas, where condensation of water from the sterilization atmosphere during the sterilization process is substantially prevented. The inventive sterilization method includes providing a sterilization chamber and placing an article into the sterilization chamber. The sterilization chamber is sealed prior to equalizing the temperature of the article and the atmosphere in the sterilization chamber. A vacuum is applied to achieve a preselected vacuum pressure in the sterilization chamber. Once the vacuum pressure is set, water vapour is supplied to the sterilization chamber. Ozone-containing gas is then supplied to the sterilization chamber and the sterilization chamber remains sealed for a preselected treatment period, where the sterilization chamber remains sealed throughout the whole process. Finally, vacuum in the sterilization chamber is released.

10 Claims, 4 Drawing Sheets

U.S. PATENT DOCUMENTS

| | | | |
|---|---|---|---|
| 4,687,635 A | | 8/1987 | Kaehler et al. |
| 4,770,851 A | | 9/1988 | Joslyn |
| 5,069,880 A | * | 12/1991 | Karlson .................. 422/186.19 |
| 5,173,258 A | * | 12/1992 | Childers ........................ 422/27 |
| 5,344,622 A | | 9/1994 | Faddis et al. |
| 5,482,683 A | * | 1/1996 | Sheth et al. .................. 422/119 |
| 5,656,246 A | | 8/1997 | Patapoff et al. |
| 5,702,669 A | | 12/1997 | Green |
| 5,868,999 A | | 2/1999 | Karlson |
| 6,284,193 B1 | | 9/2001 | Carman et al. |
| 6,325,972 B1 | | 12/2001 | Jacobs et al. |

FOREIGN PATENT DOCUMENTS

| | | |
|---|---|---|
| CA | 2443044 | 3/2005 |
| FR | 2759590 | 9/1998 |
| JP | 163244 | 10/1982 |
| JP | 7136236 | 5/1995 |
| JP | 140077 | 5/2000 |
| WO | WO 99/32162 | 7/1999 |
| WO | WO 00/66186 | 11/2000 |
| WO | WO 01/58499 | 8/2001 |

* cited by examiner

METHOD AND APPARATUS FOR OZONE STERILIZATION

RELATED APPLICATIONS

This application is a continuation-in-part of pending application Ser. No. 10/005,786, filed Nov. 8, 2001 and entitled Method and Apparatus for Ozone Sterilization, which in turn is a continuation-in-part of application Ser. No. 09/310,695, filed May 12, 1999 now abandoned.

FIELD OF THE INVENTION

The invention relates to sterilization equipment and, particularly, to a method and apparatus for ozone sterilization.

BACKGROUND OF THE INVENTION

Sterilization is the absolute destruction of any virus, bacteria, fungus or other micro-organism, whether in a vegetative or in a dormant spore state. Conventional sterile processing procedures for medical instruments involve high temperature (such as steam and dry heat) or toxic chemicals (such as ethylene oxide gas, EtO). Steam pressure sterilization has been the time-honoured method of sterilization. It is fast and cost effective. However, the autoclave destroys heat-sensitive instruments. Thus, since more and more heat-sensitive instruments such as arthroscopes and endoscopes are used in medical treatment, other types of sterilization need to be used.

Ethylene oxide sterilization is used to cold sterilize heat-sensitive instruments. Until recently, ethylene oxide sterilization was the state of the art method for cold sterilization. Ethylene oxide sterilizes heat and moisture-sensitive objects and penetrates very well. However, it has been deemed by national health and safety organizations to be carcinogenic and neurotoxic.

A more efficient, safer, and less expensive sterilization agent has been found in the form of ozone $O_3$. Ozone can easily be generated from oxygen, which is readily available in the hospital environment, usually from a wall or ceiling oxygen source, or, if mobility is required, from a portable "J" cylinder of oxygen.

Ozone generally acts on chemical compounds. Either by direct reaction or through hydroxyl radical species formed during the decomposition of ozone (Encyclopaedia Of Chemical Technology, Vol. 17, Ozone page 953 to 964). The sterilizating activity of ozone increases rapidly with increased relative humidity. The resistance of spores to ozone varies from strain to strain, but the differences become comparatively small at high relative humidity (Ishizaki et al., 1986. Inactivation of the Silas spores by gaseous ozone, J. Appl. Bacterial, 60:67-72). The presence of water often accelerates ozone reactions with organic substances (Langlais et al., (EDS), 1991, Ozone in Water Treatment, Application and Engineering. Louis Publishers: Chelsea, Mich., 569 pages).

The use of a mixture of ozone gas with a very fine water mist in a sealed plastic bag container which contains an article to be sterilized is described in U.S. Pat. No. 3,719,017. U.S. Pat. No. 5,069,880 describes a device capable of generating a high relative humidity by bubbling ozone gas through a water bath in an effort to increase the water content of the gas. However, using such a high humidity may lead to condensation of water on the articles to be sterilized. Condensation is not only undesirable, but must be avoided, since it prevents direct access of the ozone gas to organisms on the surface to be sterilized. PCT CA2002/01720, which is incorporated herein by reference in its entirety, describes an ozone sterilization method including a temperature equalization step for bringing the article to be sterilized to substantially the same temperature as the sterilization atmosphere, so that condensation is avoided as much as possible. This is achieved by multiple cycles of evacuating the sterilization chamber and re-introducing ambient air. Such a method is time consuming due to the repeated evacuation and re-filling of the sterilization chamber. Thus, an improved method is desired.

SUMMARY OF THE INVENTION

It is an object of the invention to provide a method and apparatus for the sterilization of an article with ozone-containing gas, wherein condensation of water from the sterilization atmosphere during the sterilization process is substantially prevented.

The preferred sterilization method in accordance with the invention for the sterilization of an article includes the following steps:
  a) providing a sterilization chamber;
  b) placing the article into the sterilization chamber;
  c) sealing the sterilization chamber;
  d) equalizing the temperature of the article and the atmosphere in the sterilization chamber,
  e) applying a vacuum of a preselected vacuum pressure to the sterilization chamber;
  f) supplying water vapour to the sterilization chamber under vacuum;
  g) supplying ozone-containing gas to the sterilization chamber;
  h) maintaining the sterilization chamber sealed for a preselected treatment period; and
  i) releasing the vacuum in the sterilization chamber, wherein the sterilization chamber remains sealed throughout the whole process.

Although equalization of the temperature of the article and the sterilization chamber can be achieved by simply waiting sufficiently long, this may result in an undesired delay of the sterilization procedure. Using multiple pulses of evacuation and flushing with outside air is time consuming and may introduce temperature fluctuations. Thus, temperature equalization is achieved in accordance with the present invention by sealing the chamber and equalizing the temperature while the chamber is sealed. Preferably, equalization is achieved by continuously re-circulating the air in the sterilization chamber after the chamber has been sealed. The chamber remains sealed throughout the whole process for a more reliable equalization of the temperature of the chamber and its contents.

A preferred sterilization apparatus in accordance with the invention includes
  a) a sterilization chamber;
  b) means for equalizing the temperature of the sterilization chamber, any materials placed therein, and an atmosphere in the sterilization chamber by recirculating the atmosphere in the sterilization chamber;
  c) means for supplying ozone-containing gas to the sterilization chamber;
  d) means for supplying water vapour to the sterilization chamber; and
  e) means for applying a sufficient vacuum to the sterilization chamber to lower the boiling temperature of water below the temperature inside the sterilization chamber.

BRIEF DESCRIPTION OF THE DRAWINGS

The invention will be described in more detail in the following by way of example only and with reference to the attached drawings wherein.

DETAILED DESCRIPTION OF THE PREFERRED EMBODIMENT

Figure 1:
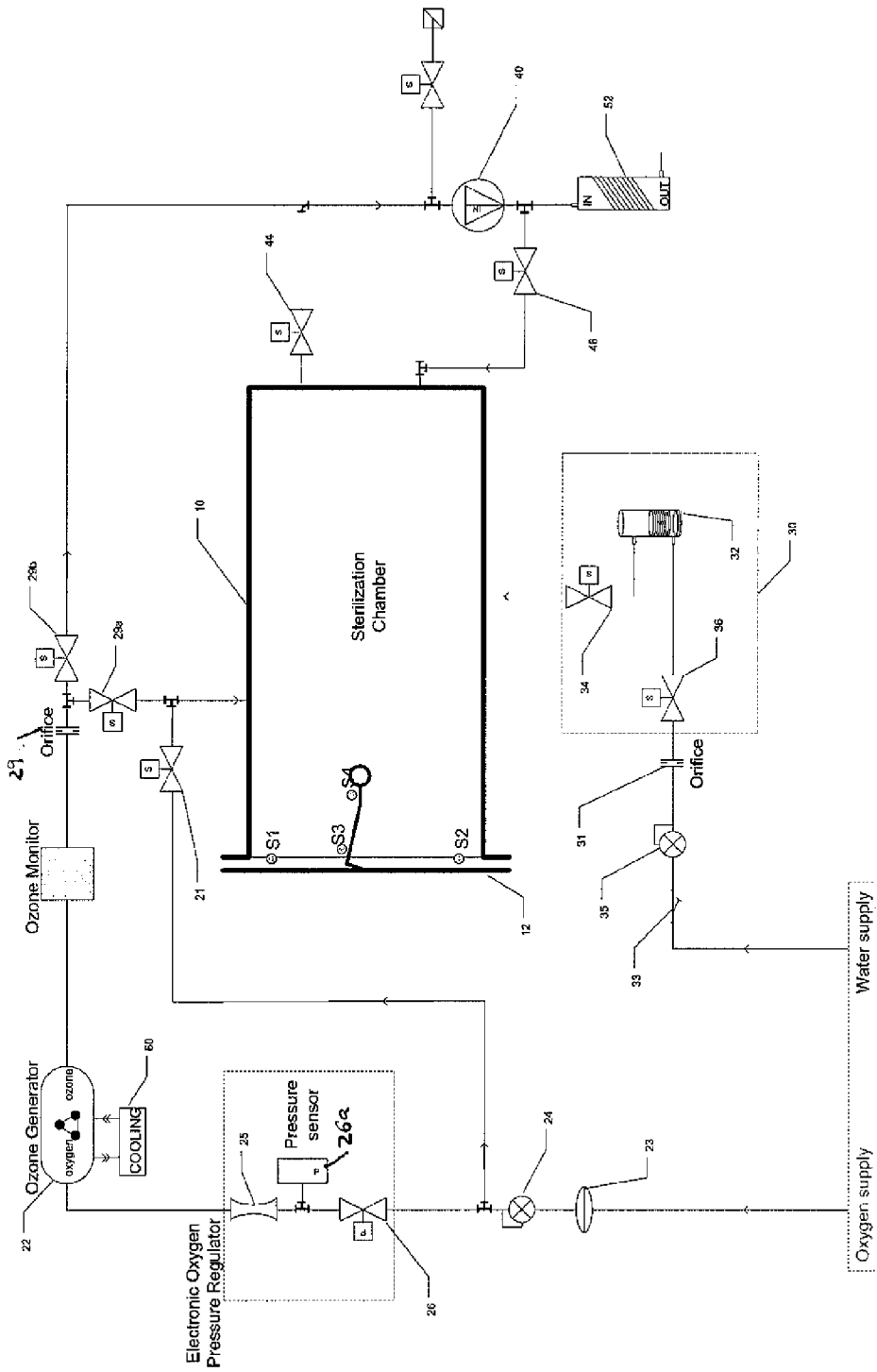
FIG. 1 shows a schematic illustration of an apparatus in accordance with the invention.

An ozone sterilizer in accordance with the invention as illustrated schematically in FIG. 1 operates in a relatively simple manner. Medical quality oxygen is subjected in an ozone generator 22 to an electrical field, which converts the oxygen into ozone containing gas. The ozone containing gas is then fed into a humidified sterilization chamber 10 where it sterilises medical devices. The ozone is subsequently reconverted into oxygen using an ozone catalyst 52. The only residues left at the end of the sterilization cycle are oxygen and clean water.

The ozone sterilization method of the invention requires substantially no aeration or cooling down of sterilized instruments so that they can be used immediately following the sterilization cycle. This allows hospitals to reduce the cost of maintaining expensive medical device inventories. The ozone sterilization method of the invention offers several further advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

The sterilization atmosphere is humidified to increase the efficiency of the ozone sterilization process. However, sterilization at the desired relative humidity of close to 100% creates additional challenges associated with unwanted condensation on articles to be sterilized. To avoid undesired condensation as much as possible, on the articles to be sterilized at least prior to ozone injection, differences in the temperature of the articles and the atmosphere in the sterilization chamber should be avoided as much as possible. PCT CA2002/01720 addresses this problem by equalizing the temperature of all materials exposed to the atmosphere in the sterilization chamber through repeated evacuation of the chamber and intermediate flushing with ambient air at ambient temperature. This is time consuming. This problem is now addressed by the method in accordance with the invention wherein temperature equalization is achieved, after the sterilization chamber has been sealed, by re-circulation of the atmosphere in the sealed sterilization chamber and without introduction of any external gases.

The preferred sterilization apparatus in accordance with the invention as illustrated schematically in FIG. 1 includes a sterilization chamber 10 which can be sealed to contain a vacuum. This is achieved with an access door 12, which can be selectively opened for access into the chamber and which seals the chamber in the closed condition. The apparatus further includes an ozone generator 22 for supplying ozone-containing gas to the sterilization chamber, a humidifier arrangement 30 for supplying water vapour to the sterilization chamber, and a vacuum pump 40 (ISP500-B, manufacturer Anest Iwata). The vacuum pump 40 is used for the application of a sufficient vacuum to the sterilization chamber 10 to increase the penetration of the sterilizing gas and to be able to generate water vapour at a temperature below the temperature inside the sterilization chamber. The vacuum pump 40 in the preferred embodiment is capable of producing a sufficient vacuum in the sterilization chamber to lower the boiling point of water in the chamber below the actual temperature of the atmosphere in the chamber. In the preferred apparatus, the vacuum pump is capable of producing a vacuum of 0.1 mbar.

Ozone produced in the ozone generator 22 is destroyed in an ozone catalyst 52 to which ozone-containing gas is fed either after passage through the sterilization chamber 10 or directly from the ozone generator 22 through valve 29b (optional). The ozone catalyst 52 (DEST 25, manufacturer TSO3) is connected in series after the vacuum pump 40 to prevent ozone gas escaping to ambient. For economic and practical reasons, it is preferred to use a catalyst for decomposition of the ozone in the sterilization gas exhausted from the sterilization chamber 10. The catalyst destroys ozone on contact and retransforms it into oxygen with a certain amount of heat being produced. Catalysts of this type and their manufacture are well known to the person skilled in the art of ozone generators and need not be described in detail herein. The ozone decomposing material in the preferred catalyst 52 is CARULITE®. Furthermore, other means for destroying the ozone contained in the sterilization gas will be readily apparent to a person skilled in the art. For example, the gas can be heated for a preselected time to a temperature at which the ozone decomposition is accelerated, for example, to 300° C.

The humidifier arrangement 30 includes a humidifier chamber 32 (HUM 0.5, manufacturer TSO3) sealed to ambient and connected to the sterilization chamber 10 through a conduit and a vapour intake valve 34. The humidifier chamber 32 is equipped with a level control to always ensure a sufficiently high water level (not shown). Water is directly supplied to the humidifier chamber 32 from a drinking or purified water supply connection. Water is supplied to the humidifier chamber 32 by way of a filter 33, a pressure regulator 35, an orifice 31 and input valve 36. The water vapour produced in the humidifier chamber 32 enters the sterilization chamber 10 by way of a vapour intake valve 34. The humidifier chamber is also preferably equipped with a heating device (not shown) that maintains the temperature of the water sufficiently high to achieve a higher water vapour evaporation rate.

The preferred ozone generator 22 for use in the apparatus of the present invention is of the corona discharge type (OZ, model 14a, manufacturer TSO3), but other ozone generators are known and will be readily apparent to the person skilled in the art. In the preferred embodiment of the apparatus of the invention, the ozone generator is cooled to decrease the ozone decomposition rate, all of which is well known in the art. To achieve a good lethality rate in an ozone sterilization process, the ozone supplied into the sterilization chamber should be sufficient to obtain a concentration of 48 to 96 milligram per liter preferably 60 to 85 milligram per liter. At these concentrations, the ozone generation is associated with a relatively high-energy loss in the form of heat. Generally, about 95% of the supplied electrical energy is converted into heat and only 5% is used to produce ozone. Since heat accelerates the inverse transformation of ozone into oxygen, it should be removed as quickly as possible by cooling of the ozone generator 22. The ozone generator in the apparatus is kept at the relatively low temperature of 4 to 6° C. by a cooling system 60 (schematically illustrated). Numerous cooling systems exist and the person skilled in the art will be able to select an appropriate cooling system for use in the apparatus of the present invention without any further description. The cooling system is preferably kept at the temperature of 4 to 6° C. In the preferred embodiment, the cooling system is kept at 4° C. so that the ozone-containing gas generated by generator 22 is at the ambient temperature of around 20 to 35° C. Thus, the ozone-containing gas entering into the sterilization chamber for humidification and sterilization is kept at ambient temperatures of 20 to 35° C. This means that ozone decomposition is minimized and that the sterilization process is more efficient.

The ozone-generator is preferably supplied with medical grade oxygen from a wall oxygen outlet common in hospitals or from an oxygen cylinder or from any other source capable of supplying the required quality and flow. The supply of oxygen to the ozone generator 22 takes place across a filter 23 and an electronic oxygen pressure regulator which includes a proportional valve 26 a pressure sensor 26a and a flow meter 25. a pressure regulator 24, a flow meter 25 and an oxygen shut off valve 26. The generator is protected against oxygen over pressure by the electronic oxygen pressure regulator. The ozone-oxygen mixture generated by the generator 22 is directed to the sterilization chamber 10 by a regulator valve 28 and a mixture supply solenoid valve 29a. The mixture can also be directly supplied to the ozone catalyst 52 by way of a bypass solenoid valve 29b (optional). In the preferred embodiment which includes a sterilization chamber of 125 liters volume, the pressure regulator 24 and the orifice 28 preferably control the oxygen input at a pressure of about 116.5 kPa (2.2 psig) and a flow rate of about 1.5 liters per minute. However, it will be readily apparent to the skilled person that other flow rates may be used depending on the make and model of the ozone generator 22 and the size of the sterilization chamber.

Temperature equalization is carried out by way of vacuum pump 40, sterilization chamber drainage valve 44 and recirculation valve 46.

The vacuum in the sterilization chamber 10 is produced by the vacuum pump 40 and chamber drainage valve 44.

Valve 26 is preferably 013 A 5/32 FPM ss npt 1/4 (manufacturer: Burkert). Valves 29a and 29b are Teflon solenoid valves (model: M442C1AFS-HT-1mic, manufacturer: Teqcom). Valve 34 (CV25-K2K2-ECNSS-24DC) is preferably a solenoid valve which is the same model as the chamber drainage valve 44 and recirculation valve 46 (manufacturer: Varian).

Operation

Figure 2:
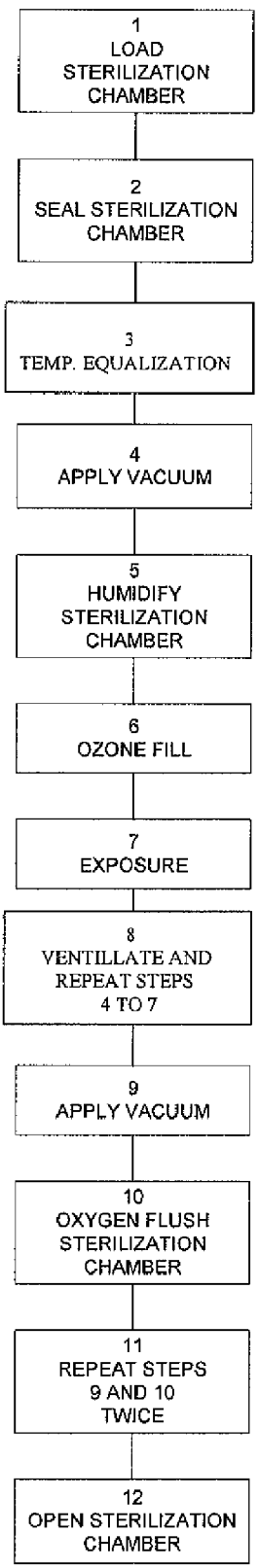
FIG. 2 is a flow diagram of a preferred method in accordance with the invention.
Figure 4:
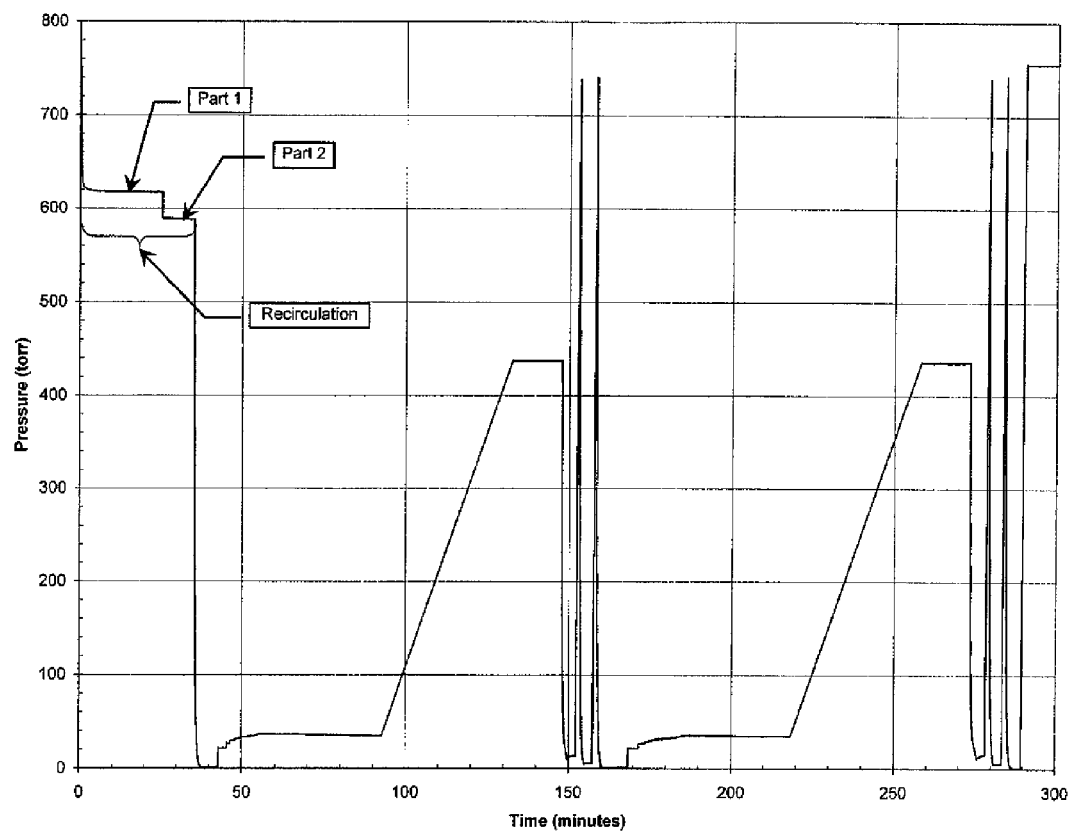
FIG. 4 is a pressure graph of a preferred sterilization process in accordance with the invention.

The preferred sterilization method according to the invention includes the following general steps as illustrated by the flow chart of FIG. 2. The medical instruments to be sterilized are sealed in sterile packaging containers or pouches such as generally used in the hospital environment and then placed into the sterilization chamber. The door of the sterilization chamber is closed and locked and the temperature equalization phase is started. This phase includes re-circulation of the atmosphere in the chamber as will be described in more detail below. Then, vacuum is applied to the sterilization chamber. Water vapour is admitted into the sterilization chamber to humidify the chamber contents. A mixture of ozone and oxygen is supplied to the chamber and the chamber maintained sealed for a preselected treatment period. The vacuum application and ozone supply steps are preferably repeated at least once after a ventilation step, as shown in FIG. 4. To remove all remaining ozone in the sterilization chamber 10 after the sterilization process is completed, a ventilation phase is commenced. After the ventilation phase the door is unlocked and the sterilized articles can be removed from the chamber. The temperature of the bottom and door of the chamber, of the water vapour piping and of the humidifier is preferably controlled throughout the sterilization process.

When the sterilization chamber is loaded, the load (cart, instruments, containers, pouches) is not at the same temperature as the chamber walls. The load is almost always colder than the walls. At certain steps of the sterilization cycle the relative humidity inside the chamber is very high (above 90%). A temperature differential between chamber walls and the load will cause water condensation on the load and that is to be avoided as much as possible. Temperature equalization can be achieved by cooling the chamber walls, or warming up the load. In the process of the invention, the temperature differences are equalized by recirculation of the atosphere in the sterilization chamber, which means at the beginning of the sterilization process (FIG. 1). The vacuum pump 40 is used to recirculate air inside the chamber.

When the sterilization process is started, the door is locked, the vacuum pump starts, and chamber drainage valve 44 as well as recirculation valve 46 are opened (step 3 in FIG. 2). The air trapped inside the chamber is sucked by the vacuum pump through the chamber drainage valve 44. By pumping air out of the chamber, the pressure inside the chamber decreases. Thus, since the recirculation valve 46 is also open, a major part of the air exiting the vacuum pump is sucked back into the sterilization chamber through the recirculation valve 46. A minor part of the evacuated air is flowing through the catalyst 52 to the exhaust (OUT).

Running at or close to atmospheric pressure, the vacuum pump 40 circulates the atmosphere in the chamber 10 at a high flow (approximately 475 l/min according to manufacturer specifications). This results in a high air flow rate through the chamber 10 and equalization of any temperature differences between the load, the chamber and the air. As a side effect of the recirculation by way of the vacuum pump, the air is also heated by the action of the pump (in the exemplary embodiment air exited the pump at 55-65° C.).

In order to increase the reliability of the recirculation step, the recirculation step is preferably divided into two parts (FIG. 4). In the first part, the air is re-circulated for 10 minutes. In the second part, which preferably lasts for 20 minutes, there is no recirculation, since the chamber drainage valve 44 and the recirculation valve 46 are both closed at the end of the first part. The total duration of the recirculation process is thus 30 minutes.

During the recirculation process only the duration of the first and second parts is controlled, while all other parameters (air flow, air temperature, pressure inside the chamber) need neither be monitored nor controlled. Although the nominal throughput of the vacuum pump 40, the valves 44 and 46 and the other components of the recirculation circuit is constant, the actual air flow through the pump and the chamber depends on the pressure drop generated by the load in the chamber. Furthermore, although a heating of the pumped air will occur with any vacuum pump, the degree of heating will depend of the air flow and the friction inside the vacuum pump, which may vary from one pump to another. During the first part of the recirculation step, the pressure inside the chamber is initially decreasing and then stabilizes, when the maximum air flow is achieved. By evacuating air through the chamber drainage valve 44, the pressure in the chamber is decreased, but this lower pressure also pulls air exiting the vacuum pump back into the chamber through the recirculation valve 46. Eventually, the pressure stabilizes naturally and the actual pressure level depends on the amount of the load and its placement in relation to the inlet or outlet ports in the chamber. In the exemplary sterilizer apparatus in accordance with the invention, the pressure generally stabilized between 766 and 886 mbar. In the pressure graph of FIG. 4, the chamber pressure once again decreases upon the transition form the first to the second part of the recirculation cycle. This was caused in the exemplary apparatus by the recirculation valve 46 closing about 0.5 seconds before the chamber drainage valve 44. The pressure during the second part was lower by approximately 25 torr. At the end of the temperature equalization step, the chamber drainage valve 44 is once again opened and the vacuum pump 40 operated until the desired sterilization vacuum is reached (see FIG. 4).

Before the sterilization cycle begins, the humidifier chamber 32 is filled with water to an adequate level. This is done by temporarily opening the water-input valve 36. Water level control valve 36 also preferably opens automatically during the sterilization cycle if the water level is dropping below a preselected limit.

At the onset of the sterilization cycle, a vacuum is applied to the sterilization chamber (see step 4 in FIG. 2). The sterilization chamber 10 is evacuated to a vacuum pressure of about 1.0 mbar. Water vapour inlet valve 34 is closed when the absolute pressure in the sterilization chamber falls below 60 mbar. Once a pressure of about 1.0 mbar is achieved, the chamber drainage valve 44 is closed and the vapour intake valve 34 opened to lower the pressure in the humidifier chamber 32 to the vacuum pressure in the sterilization chamber. That forces the water in the humidifier chamber to evaporate with the resulting water vapour automatically entering the sterilization chamber 10 due to the volume increase associated with the transition of the water from the liquid to the gaseous phase. Preferably, during the humidification period, valve 34 opens and closes several times for a pre-set period of time to control the increasing rate of the relative humidity inside the chamber. Instead of using a humidifier chamber, humidity introduction into the chamber could also be achieved with one or more spray nozzles connected to the water supply line, or through pulsed water injection (small amounts of water injected each time). When valve 34 opens the pressure of the water flowing through the nozzle produces a water fog that evaporates into the volume under vacuum. Shortly before the end of the humidification period (usually about 2 to 6 min.), the ozone generator is activated. The flow of the oxygen/ozone mixture exiting the ozone generator is controlled at all times by regulator valve 28 capable of resisting the vacuum and of adjusting the flow to between 1 and 3 liters per minute. As an optional feature, the generator can be started at the same time as the humidification period begins. This is then achieved with supply valve 26 and mixture bypass valve 29b. supply valve 26 opens to let oxygen enter the generator. The ozone-oxygen mixture produced by the generator is then guided directly into the ozone catalyst 52 through mixture bypass valve 29b. After a humidification period of 30 to 90 minutes, the oxygen-ozone mixture is guided into the sterilization chamber by opening the mixture supply valve 29a and closing the mixture bypass valve 29b. The oxygen-ozone mixture enters the chamber 10 until an ozone concentration of 85 milligram per liter in the chamber is achieved. The time required for this step is dependent on the flow rate and concentration of the ozone gas in the mixture (preferably 150 to 190 mg/l NTP) and the ozone concentration can be monitored with equipment known in the art. Once the desired concentration is reached, the mixture supply valve 29a is closed to seal off the sterilization chamber and to maintain the humidified ozone/oxygen gas mixture in the chamber under vacuum.

Once the sterilization chamber is filled with the sterilization gas (mixture of oxygen and ozone gas), the generator 22 is stopped, the oxygen supply valve 26 is closed, and the ozone is maintained in contact with the articles to be sterilized for about 20 minutes, for a sterilization chamber of a volume of 125 liters (4 cubic feet). The length of the sterilization period varies with the volume of the sterilization chamber. At this stage, the sterilization chamber is still under the effect of a partial vacuum of about 610 mbar. In an optional second step, the pressure level is raised to about 900 mbar using oxygen as a filling gas. This pressure level is maintained for about 20 min. After the sterilization period, the vacuum is reapplied, preferably at a pressure of about 1.0 mbar again. Once the vacuum reaches 1.0 mbar, the humidification phase is recommenced, followed by the renewed injection of an oxygen/ozone sterilization gas mixture, followed by the sterilization period. The cycle of applying a vacuum of about 1.0 mbar, injecting sterilization gas, humidifying and sterilization period, can be repeated, and the number of repeat cycles (mini cycles) selected to achieve complete sterilization of the instruments. The number of repeat cycles needed in an experimental set-up of a method and apparatus in accordance with the invention including a 125 liters (4 cubic foot) chamber was 2. This set-up conformed to the Security Assurance Level standards of the FDA (SAL 10-6).

To remove all remaining ozone and humidity in the sterilization chamber 10 after complete sterilization a ventilation phase is engaged. The ventilation phase begins after the last sterilization period. The chamber drainage valve 44 is opened and a vacuum is applied down to approximately 6.5 mbar. Vapour intake valve 34 closes when the pressure reaches 60 mbar to evacuate the remaining ozone in the humidifier. Once the vacuum pressure of 6.5 mbar is obtained, drainage valve 44 closes and the oxygen supply valve 21 opens, admitting oxygen into the sterilization chamber 10. Once atmospheric pressure is reached, the oxygen supply valve 21 is closed, the sterilization chamber drainage valve 44 is opened, and vacuum reapplied until a pressure of 1.3 mbar is reached. This last ventilation cycle, down to 1.3 mbar, is repeated once for a total of three ventilation cycles. Once atmospheric pressure is reached after the last cycle, the door mechanism of the sterilization chamber is activated to permit access to the contents of the sterilization chamber. The ventilation phase has two functions. First, to remove all ozone residues in the sterilization chamber before opening the access door and, second, to dry the sterilized material by evaporation when the vacuum pressure is applied. Of course, different vacuum pressures, cycle times and number of repetitions can be used, as long as the desired ozone removal and drying are achieved.

The ozone-containing gas evacuated from the sterilization chamber 10 is passed over the ozone catalyst 52 prior to exhausting the gas to the atmosphere to ensure a complete decomposition of the ozone in the sterilization gas. The ozone catalyst 52 is used during only two portions of the sterilization cycle, the activation of the generator 22 (with optional valves 26 and 29b) and the evacuation of the sterilization chamber 10. During the start up phase of the generator 22, the mixture bypass valve 29b is opened and the ozone is guided across the catalyst 52. Once the start-up phase of the generator 22 is complete, the bypass valve 29b closes. During evacuation of the sterilization chamber 10, the sterilization chamber drainage valve 44 is opened and the ozone containing sterilization waste gas is guided to the catalyst 52. Once the evacuation of the sterilization chamber 10 is completed, the drainage valve 44 is closed. The circulation of ozone is ensured by the vacuum pump 40. The ozone catalyst 52 can be located upstream or downstream of the vacuum pump 40.

Control System

Figure 3:
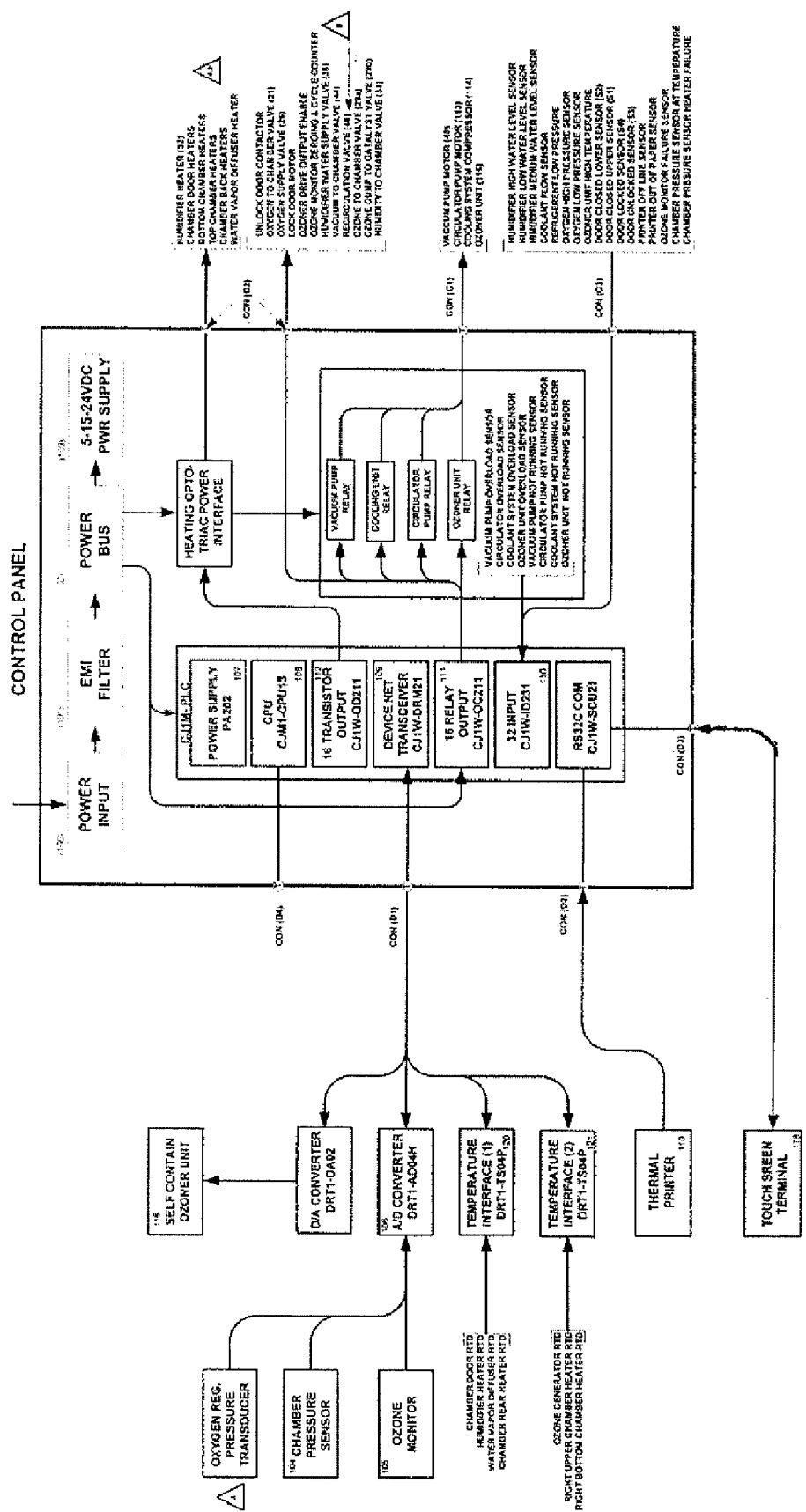
FIG. 3 is a flow diagram of the electrical and control system preferably used in the apparatus of FIG. 1.

The sterilization apparatus is preferably controlled by the scheme presented in the electrical block diagram (FIG. 3) and Process Flow Diagram (FIG. 2). The control system is build around a PLC shelf (Programmable Logic Controller). This shelf contains a power supply (107) a CPU unit (108), a Device Net Transceiver (109), a 32×24 volts DC discrete input module (110), a 16×120VAC discrete output module (111) and finally an 8×120VAC TRIAC controlled output module (112). All those modules are disposed on a physical shelf that contains a data and address bus.

Device Net is an industrial serial communication protocol largely used in the industry for instrumentation and control. In this sterilization apparatus the Device Net transceiver (109) is used to communicate in full duplex, the data between the CPU (109) and the 15 bit A/D converter (106) and both Digital Temperature Interfaces (120), (121).

The PLC CPU posses three RS232 ports. One is used to receive and send data to the Touch Screen Terminal (118), another one is used to send data to a thermal printer (119) and the last port is used as a service port where a PC (Personal Computer) can be hooked up to communicate with the PLC CPU (108) to load up the control protocol program. (Control Protocol Program is not in the scope of this document).

The Touch Screen terminal (118) is located at the front of the sterilizer beside the thermal printer (119). Touch Screen Terminal and thermal printer constitute a User Interface terminal.

Power needed for: "thermal printer (119), Device Net Link, (109), (106), (120), (121), Chamber Pressure Sensor (104) and PLC discrete inputs (111)" come from the DC Power supply (103).

Chamber Pressure Sensor (104) and Ozone Monitor (105) have standard 0 to 10VDC output signal. Both signals are sent to a 15 bits A/D converter. Then, both converted signals are sent to CPU by the Device net digital link for processing.

Power input (100) of the sterilizer is a four wire 208 VAC 3 phases in star configuration with neutral. The 3 phase power input is filtered to prevent conducted RFI (101). Then, power is distributed by power distribution buss (102) to the various electrical systems of the sterilizer apparatus.

A cooling system (60) is used to cool down the ozone generator. This system include the cooling unit (114) and the coolant circulator pump (113). The temperature of the coolant in the generator is sense by an RTD located at the generator. The temperature is sent to the CPU (108) by the Device Net system (109) (120) (121). Coolant circulator (113) and cooling unit (114) are controlled by contactors driven by PLC outputs (111) which in turn are controlled of the software protocol. All input and output required to achieve cooling system control are listed on the electrical block diagram as: Circulator Pump Contactor, Cooling System Contactor, Circulator Overload Sensor, Cooling System Overload system, Coolant System Not Running Sensor, Circulator pump Not Running Sensor. Refrigerent Low Pressure and Coolant Flow Switch.

The vacuum control system includes the vacuum pump 40 and a pressure sensor 104. The start and stop operations of the vacuum pump are controlled according to the control protocol. All input and output required for the vacuum system is listed on the diagram: Vacuum Pump Contactor, Vacuum Pump not running sensor, Vacuum pump Overload sensor, Vacuum to Chamber valve (44), Recirculation Valve (46) and Oxygen to Chamber valve (21). The pressure sensor output is converted by the 15 bit A/D converter (106) and sent to the CPU by the Device Net digital Link (109). The pressure sensor also posses two discrete outputs indicating to the CPU (108) the following conditions: Chamber Pressure Sensor at Temperature and Chamber Pressure Sensor Heater failure. Those two signals are listed on the electrical block diagram as PLC inputs.

The sterilization chamber door actuator system includes an electric drive of the screw type and four inductive sensors which allow the detection of the presence of the door and the locked or unlocked position of the actuator as part of the control protocol. The door opening system is also used in the alarm conditions management protocol to assure the safety of the user. All input and output required to achieve the door actuator system are listed on the electrical block diagram as: Lock Door Contactor, Unlock Door Contactor, Door closed Lower Sensor (S2), Door closed Upper Sensor (S1), Door Locked Sensor (S4) and Door Unlocked Sensor (S3).

The Ozone power supply (116) includes a full wave rectifier, an oscillator circuit and a high voltage transformer. The output of the transformer is hooked up to the ozone generator (22). The power supply (116) is mounted as a resonator using the non-ideal characteristics of the high voltage transformer. The PLC 108 controls the ozone production by way of a feedback control loop and ensures by way of the ozone monitor 104 and the D/A converter 123 that the concentration desired for sterilization is achieved and maintained throughout the sterilization cycle. All input and output required by the Ozone Generation System is listed on the diagram as: Oxygen Supply Valve (26), Ozone to Chamber valve (29a), Ozone Dump to Catalyst valve (29b), Ozone Monitor Zeroing & Cycle counter, High Voltage Control, High Voltage Current Limiter, Ozone High Voltage Overload sensor Rectifier High Temperature Sensor, Ozone High Voltage Not Running Sensor and Ozone monitor Failure Sensor.

Ozone to Chamber valve (29a) and Ozone Dump to Catalyst valve (29b) are driven by an Electronic Solenoid Power Damper (117). This apparatus prevents over-heating of the valves.

The oxygen supply system includes the electronic oxygen pressure regulator including a proportional valve 26 a pressure sensor 26a and a flow meter 25. The oxygen supply system further includes a valve 21 and a 350 mbar (gauge) maximum gas pressure regulator 24 for supply of oxygen directly to the chamber 10. The sensors and regulators are an integral part of the alarm condition protocol to ensure the protection of the user. Inputs used for the alarm condition are listed on the electrical block diagram as: Oxygen High Pressure Sensor and Oxygen Low Pressure Sensor.

The control system is provided with a user interface 118. In the preferred embodiment, this interface includes a touch-sensitive liquid crystal display (LCD) screen 118, a printer 119 for performance reports and a communications port 153 (Series RS-232) allowing the user to receive and transmit information necessary for use of the apparatus. It will be readily apparent to the person skilled in the art that other types of user interfaces can be used such as touch-sensitive pads, keyboards, or the like, and other types of communications interfaces. Thermal printer status inputs appear on the electrical block diagram as: Printer Off Line Sensor and Printer Out of Paper.

The system in accordance with the invention is capable of producing a relative humidity level higher than 95%.

The energy needed to evaporate the water during the humidification phase is taken from many sources. It is taken principally from the water and the structure of the humidifier unit. This contributes to a further cooling of the humidifier, and its contents. In effect, at 20° C., water boils up to an absolute pressure of 23.3 mbar and at 35° C., water boils up to an absolute pressure of 56.3 mbar. The vacuum in the sterilization chamber is preferably adjusted at a pressure where the boiling temperature of water is lowered below the temperature in the sterilization chamber. That boiling temperature may be so low that the temperature of water inside the humidifier decreases rapidly and, depending on the energy available from the surrounding structure and liquid, the water in the humidifier chamber may freeze before it gets vaporized. The evaporation process cooled the humidifier to a point where room air moisture condenses and may also freezes to the external surface of the humidifier. This can be avoided in another preferred embodiment by heating the external surface of the humidifier sufficiently to keep the exterior of the humidifier unit and the water inside the humidifier chamber at room temperature. This is achieved with a heating arrangement (not illustrated) which will be readily apparent to the person of skill in the art. Also, because of the high level of relative humidity achieved inside the chamber there is condensation on chamber inner surfaces and inside water vapour piping. To reduce water condensation the bottom of the chamber, the door and the water vapour piping also heated.

The water vapour generated in the humidifier unit increases the relative humidity in the sterilization chamber. The humidification phase is continued until the relative humidity of the gas surrounding the medical instruments contained in the packaging pouches and containers reaches a minimum of 85%, preferably 100%. For a sterilization chamber of an approximate volume of 125 liters, the water vapour admission increases the pressure to about 50 mbar in the sterilization chamber. This value is an approximation because it is temperature dependent.

Oxygen/ozone-containing sterilization gas is injected into the humidified sterilization chamber at a temperature close to ambient. The ozone-containing gas is not heated as in the prior art. For optimum operation of a sterilizer in accordance with the invention and having a 125 liters chamber, a system is preferably used which is capable of generating an ozone flow of about 1 to 3 liters per minute containing about 85 mg/l of ozone to obtain at least a total of 10600 mg of ozone for each of the fillings of the sterilization chamber.

In another preferred process, humidification of the sterilization chamber is carried out by a pair of atomizers. The water is supplied to each of the atomizers from a water tank hooked up to the drinking water supply or a purified water supply. Ozone is supplied to the atomizers from an ozone accumulation tank. The atomizers are made of ozone oxidation resistant material, and are installed directly in the sterilization chamber. When the vacuum level is reached in the sterilization chamber, the atomizers release water and ozone. The ozone is moistened inside the atomizer. The ozone/atomized water mixture penetrates the sterilization chamber. Injecting the water into the sterilization chamber under vacuum has the immediate effect of evaporating the water. The sterilization chamber operating temperature is 25 to 40° C., a temperature at which water evaporates at pressures of 31.7 to 73.8 mbar. Thus, the water becomes vapour due to the vacuum created by the vacuum pump. The resulting ozone/water vapour mixture penetrates the material to be sterilized.

Changes and modifications in the specifically described embodiments can be carried out without departing from the scope of the invention which is intended to be limited only by the scope of the appended claims.

What is claimed is:

1. A method for sterilizing an article in a sterilization gas atmosphere, comprising the steps of:
    a) providing a sterilization chamber;
    b) placing the article into the sterilization chamber;
    c) sealing the sterilization chamber;
    d) evaporating water on the article and equalizing the temperature of the article and an atmosphere in the sterilization chamber for equalizing any localized cooling of the article caused by the evaporation of water on the article, by evacuating the atmosphere in the sterilization chamber and re-circulating a major portion of the evacuated atmosphere into the chamber, while exhausting a minor portion of the evacuated atmosphere to ambient for gradually reducing a pressure in the chamber;
    e) terminating the re-circulating and reducing the pressure in the sterilization chamber to a vacuum sufficient to lower the boiling point of water to a temperature of an atmosphere in the chamber;
    f) humidifying the atmosphere in the chamber by supplying water to the sterilization chamber under the vacuum;
    g) supplying ozone-containing gas to the sterilization chamber;
    h) maintaining the sterilization chamber sealed for a preselected treatment period; and
    i) releasing the vacuum in the sterilization chamber, wherein the sterilization chamber remains sealed from step c) to step i) of the process.

2. The method of claim 1, wherein the equalizing step comprises a first part in which the atmosphere is evacuated and a second part in which the evacuation is interrupted and the pressure in the chamber is maintained.

3. The method of claim 1, wherein the equalization temperature in the sterilization chamber is between 25 to 60° C.

4. The method of claim 3, wherein the equalization temperature in the sterilization chamber is between 25 to 350° C.

5. The method of claim 3, wherein the equalization temperature in the sterilization chamber is between 40 to 60° C.

6. The method of claim 1, wherein the vacuum pressure is between 0.1 and 10 mbar.

7. The method of claim 6, wherein the vacuum pressure is between 0.5 and 2 mbar.

8. The method of claim 7, wherein the amount of water vapour supplied is selected to achieve a level of humidity of at least 95%.

9. The method of claim 1, wherein during step c) the temperature of the evacuated and recirculated air increases and the relative humidity of the evacuated air decreases.

10. The method of claim 1, wherein the amount of water vapour supplied is selected to achieve a level of humidity in the sterilization chamber of 85 to 100%.

* * * * *

UNITED STATES PATENT AND TRADEMARK OFFICE
CERTIFICATE OF CORRECTION

PATENT NO. : 7,588,720 B2  Page 1 of 1
APPLICATION NO. : 11/554763
DATED : September 15, 2009
INVENTOR(S) : Richard Turcot et al.

It is certified that error appears in the above-identified patent and that said Letters Patent is hereby corrected as shown below:

Column 12, line 40, delete "350" and insert therefor --35--.

Signed and Sealed this

Fifth Day of January, 2010

David J. Kappos
*Director of the United States Patent and Trademark Office*